United States Patent [19]
Nichols

[11] Patent Number: 6,127,603
[45] Date of Patent: Oct. 3, 2000

[54] **PLANT CELLS AND PLANTS TRANSFORMED WITH *STREPTOCOCCUS MUTANS* GENE ENCODING GLUCOSYLTRANSFERASE C ENZYME**

[75] Inventor: Scott E. Nichols, Johnston, Iowa

[73] Assignee: Pioneer Hi-Bred International, Inc., Des Moines, Iowa

[21] Appl. No.: 09/009,620

[22] Filed: Jan. 20, 1998

Related U.S. Application Data

[63] Continuation of application No. 08/485,243, Jun. 7, 1995, Pat. No. 5,712,107.

[51] Int. Cl.$^7$ ........................... C12N 15/31; C12N 15/54; C12N 15/82; C12P 19/04; A01H 5/00
[52] U.S. Cl. ........................ 800/284; 800/287; 800/288; 800/292; 800/293; 800/294; 800/317.2; 800/320; 800/320.1; 800/320.2; 800/320.3; 435/69.7; 435/69.8; 435/101; 435/193; 435/412; 435/417; 435/418; 435/419; 435/468; 435/469; 435/470
[58] Field of Search ................................. 435/69.1, 69.7, 435/69.8, 101, 172.3, 418, 419, 468, 469, 470, 193, 412, 417; 800/205, 250, 255, DIG. 42, 55–58, 284, 287, 288, 292, 293, 294, 317.2, 320, 320.1, 320.2, 320.3

[56] References Cited

U.S. PATENT DOCUMENTS

| | | | |
|---|---|---|---|
| 4,202,966 | 5/1980 | Misaki et al. | 536/1.11 |
| 4,342,601 | 8/1982 | Yin | 536/123.12 |
| 4,597,830 | 7/1986 | April et al. | 536/123.12 |
| 4,734,162 | 3/1988 | Ampulski | 536/123.12 |
| 5,354,424 | 10/1994 | Rha | 162/135 |
| 5,679,880 | 10/1997 | Curtiss, III et al. | 800/205 |
| 5,712,107 | 1/1998 | Nichols | 435/278.4 |
| 5,712,135 | 1/1998 | D'Halluin et al. | 435/172.3 |
| 5,985,666 | 11/1999 | Loiselle et al. | 435/419 |

FOREIGN PATENT DOCUMENTS

| | | | |
|---|---|---|---|
| 06 287 887 | 11/1994 | Japan . | |
| 06 313 297 | 11/1994 | Japan . | |
| 1122354 | 8/1968 | United Kingdom . | |
| WO 95/13389 | 11/1993 | WIPO | C12N 15/82 |
| WO 94/11520 | 5/1994 | WIPO | C12N 15/82 |
| WO96/06173 | 8/1994 | WIPO | C12N 15/54 |
| WO 97/29186 | 2/1997 | WIPO . | |
| WO 97/47806 | 12/1997 | WIPO | D21H 17/00 |
| WO 97/47808 | 12/1997 | WIPO | D21H 17/00 |

OTHER PUBLICATIONS

Gordon–Kamm, et al. "Transformation of Maize Cells and Regeneration of Fertile Transgenic Plants" *The Plant Cell*; vol. 2; pp. 603–618; (1990).

Gordon–Kamm, et al. "Transformation of Maize using Microprojectile Bombardment: An Update and Perspective" *In Vitro Cellular and Developmental Biology Plant 27P*; vol. 1; pp. 21–27; (1991).

Walbot & Messing "Gene Expression in Corn" *Corn and Corn Improvement*; Sprague and Dudley editors. 3$^{rd}$ edition (1988), pp. 418–421.

Schopke, et al. "Transformation in Cassava" *Biotechnology in Agriculture and Forestry*; vol. 23; pp. 273–289 (1993).

Lowe, et al. "Genetic Transformation in *Ipomoea batatas* (L.) Lam (Sweet Potato)" *Biotechnology in Agriculture and Forestry*, vol. 29; pp. 308–320 (1994).

Juboory, et al. "In Vitro Regeneration of Agrobacterium–Transformed Sweet Potato (*Ipomoea batatas* L.)" *PGRSA Quarterly*; vol. 19, No. 2, pp. 82–89 (1991).

Prakash, et al. "Genetic transformation of sweet potato by particle bombardment" *Plant Cell Reports*; vol. 11, pp. 53–57 (1992).

Chen, et al. "Transformation of sugarcane protoplasts by direct uptake of a selectable chmaeric gene" *Plant Cell Reports*; vol. 6, pp. 297–301 (1987).

Weising, et al. "Foreign Genes in Plants: Transfer, Structure, Expression, and Applications" *Annual Rev. Genetic*; vol. 22, pp. 421–477 (1988).

Birch, et al. "Transformation of Sugarcane" *Biotechnology in Agriculture and Forestry*; vol. 23; pp. 348–360 (1993).

Chowdhury, et al. "Stably transformed herbicide resistant callus of sugarcane via microprojectile bombardment of cell suspension cultures and electroporation of protoplasts" *Plant Cell Reports*; vol. 11; pp. 494–498 (1992).

Xu–Yao, et al., "Interaction and Transformation of Cereal Cells with Phenolics pretreated *Agrobacterium tumefaciens*" *Chinese J. Bot.*; vol. 2 (2); pp. 81–87 (1990).

Fromm, et al. "Inheritance and Expression of Chimeric Genes in the Progeny of Transgenic Maize Plants" *Bio/Technology*; vol. 8; pp. 833–839 (1990.

Honda, O., et al. "Nucleotide sequence of the *Streptococcus mutans* gtfD gene encoding the glucosyltransferase–S enzyme" J. of General Microbiology (1990)136, 2099–2105.

Napoli et al. "Introduction of a Chimeric Chalcone Synthase Gene into Petunia Results in Reversible Co–Suppression of Homologous Genes in trans" The Plant Cell (Apr. 1990) 2, 279–289.

von Schaewen, et al. "Expression of a yeast–derived invertase in the cell wall of tobacco and Arabidopsis plants leads to accumulation of carbohydrate and inhibition of photosynthesis and strongly influences growth and phenotype of transgenic tobacco plants" The EMBO Journal (1990) vol. 9 No. 10, pp. 3033–3044.

(List continued on next page.)

*Primary Examiner*—David T. Fox
*Attorney, Agent, or Firm*—Pioneer Hi-Bred International, Inc.

[57] ABSTRACT

The present invention provides methods of making paper utilizing glucans, produced by the glucosyltransferase C enzyme of the species *Streptococcus mutans*, instead of modified starches. The present glucans are functionally similar to the hydroxethyl modified starch and are particularly useful in the coating step of paper manufacture. The present glucans also exhibit thermoplastic properties and impart gloss to the paper during the coating step. In particular, the present invention provides plant cells and plants transformed with the *Streptococcus mutans* gene encoding the glucosyltransferase C enzyme.

9 Claims, No Drawings

OTHER PUBLICATIONS

Kossman, et al. "Transgenic plants as a tool to understand starch biosynthesis" Carbohydrate Bioengineering (1995), Petersen et al., eds., Elsevier Science, pp. 271–278.

Ueda et al. Sequence analysis of the gftC gene from *Streptococcus mutans* GF–5, Gene. 69 (1988) pp. 101–109.

Yao et al. Chinese J. Bot. 2(2): 81–87, Dec. 1990.

Ueda et al. Gene 69: 101–109, 1988.

Birch et al. pp. 348–360 In: Biotechnol. Agric. For., vol. 23, Bajaj, Y., ed., Springer–Verlag: Berlin, 1993.

Lowe et al. pp. 308–320 In: Biotechnol. Agric. For., vol. 29, Bajaj, Y., ed., Springer–Verlag: Berlin, 1994.

Schopke et al. pp. 273–289 In: Biotechnol. Agric. For., vol. 23, Bajaj, Y., ed., Springer–Verlag: Berlin, 1993.

Hannah et al. pp. 624–629 In: The Maize Handbook, Freeling et al., eds., Springer–Verlag: New York, 1994.

Napoli et al. Plant Cell 2: 279–289, Apr. 1990.

von Schaewen et al. EMBO J. 9(10): 3033–3044, 1990.

Kossman et al. Carbohydrate Bioengineering, Petersen et al., eds., Elsevier Science, pp. 271–278, 1995.

Guan, H.P. et al. "Expression of Branching Enzyme I on Maize Endosperm in *Eschericia coli*" (1994) Plant Physiology 104:1649–1453.

PLANT CELLS AND PLANTS TRANSFORMED WITH *STREPTOCOCCUS MUTANS* GENE ENCODING GLUCOSYLTRANSFERASE C ENZYME

This application is a continuation of U.S. patent application Ser. No. 08/485,243 filed Jun. 7, 1995, now U.S. Pat. No. 5,712,107.

FIELD OF THE INVENTION

The present invention involves the field of paper manufacture. Specifically, the present invention provides sources alternative to modified starch in paper manufacture.

BACKGROUND OF THE INVENTION

There are three major phases in paper manufacture where starch is used as an ingredient. The first is the "wet end" where cellulose fibers are mixed with starch in a slurry, and the slurry is forced through a narrow opening onto a wire belt. Water is rapidly removed as the forming sheet travels the length of the belt. After a distance of typically five to fifteen meters on the belt, the sheet has had enough water removed from it so that it can support its own weight. The sheet travels through a number of foils and rolls wherein more water is removed. It is dried to about 11% moisture.

The second phase in paper manufacturing involving starch is the "sizing step". Here, the paper goes through a sizing press where a starch slurry is applied to the sheet. The sheet again goes through a series of foils and rolls. It is dried on rollers and can be taken off the press as a finished product.

The third step involves coating the paper with a mixture of starch and a thermoplastic molecule. On certain lines, this occurs after the sizing step. The nascent roll can also be removed and reinstalled onto a different press for coating. A typical coating device has two blades that run the width of the paper. The blades apply the coating material onto two rolling drums. The paper passes between the drums and the coating material, comprising starch and the thermoplastic moiety, comes off the drums onto the paper. After the paper leaves the drums, it goes through a number of dryers. When the paper is dry, it goes onto a "soft calendar" comprising two drums, one made of a hard density fabric and the other a heated steel drum. The paper passes between the two drums and the heated steel drum is sufficiently hot to melt thermoplastic components of the coating mix providing a hard gloss finish on the paper.

The cellulosic wood pulp fibers, typically used in the above process, are anionic in nature. The addition of a cationic starch to the "wet end" slurry acts as an adhesive by cross linking the pulp fibers through salt linkages. Thus a cross linked polymeric network is made, comprising the starch and cellulose fibers. Typically, the cationic starches used in the "wet end" are tertiary or quaternary amines. These amino groups are added to the starch by wet millers.

Surface sizing starches are used to impart both strength and smooth finish to the sheet after it leaves the "wet end". Such starches also prepare the sheet to receive the various coatings. In cheaper grades of paper and in fiberboard manufacture, sizing starches are used simply as unmodified corn starch. For high grades of paper, chemically-modified starches are used. This is important for the application of a smooth, uniform high quality surface to the paper.

There is a tendency for starches to retrograde i.e. re-form high ordered structures (both helices and crystallites) in an otherwise gelatinous starch slurry. Deposition of retrograded starch onto high quality paper causes regional inconsistencies on the paper and is unacceptable. Furthermore, retrograded starch in the sizing press may necessitate shutting the line down to clear the apparatus.

The starch most often used for sizing applications is a starch having a covalently attached neutral adduct, for instance hydroxyethyl starch. This is prepared by the reaction of ethylene oxide with starch after it is isolated at the wet milling plant. The function of the hydroxyethyl (or similar) adduct is independent of its chemical nature; rather, it serves to provide steric hindrance, inhibiting the formation of high ordered structures. This steric hindrance is critical to decrease retrogradation. The periodic protuberance afforded by the adduct disrupts the formation of higher ordered structures that leads to retrogradation.

Speed is of paramount importance in paper manufacturing. Limiting in press speed is starch consistency. Presses often run below their full capacity speeds. Depending on the application, starch slurries are between 3–15% (usually 5–6%) solids. An increase in solids would necessarily result in a decrease in the amount of water that would have to be removed from a paper sheet being manufactured. This would allow the press to work at higher speeds.

Hydroxethylated starch also forms higher ordered structures as the temperature decreases or the concentration increases. The formation of the higher ordered structures on the surface of the paper is required. After application to the sheet the starch reforms some of these higher ordered structures and creates a uniform surface that imparts structural strength and facilitates the acceptance of inks and dyes. However, the higher ordered structures should not form in the slurry nor on the application device because this necessitates shutting down the production line to clear off retrograded starch.

The function of the hydroxyethyl group is to lower the temperature and/or raise the concentration of starch at which retrogradation occurs. As the processing lines have already been optimized for a particular temperature of the starch slurry, a decrease in the tendency to retrograde would allow for a higher carbohydrate content in the slurry.

The mixture applied to the paper sheet in the coating process contains hydroxethylated starch and thermoplastic molecules. The most prevalent thermoplastic molecules used are latexes, such as styrene butadiene. The function of the hydroxethyl starch is as indicated above. The function of the thermoplastic molecule is to form a high gloss finish on the paper. This causes an increased ability to take inks and dyes and improves the resolution, in general, on the printed sheet.

Based on the foregoing, there exists a need, in paper manufacturing, for modified starch substitutes which are functionally similar to modified starch. There is a further need to provide substitutes for modified starch which are less prone to retrogradation. There is a further need to provide methods of manufacturing paper which are faster than current methods and allow presses to run closer to their full capacity speed. There is a further need to provide methods of manufacturing paper that are environmentally-friendly and do not involve input materials that require chemical processing.

It is therefore an object of the present invention to provide substitutes for modified starch which are less prone to retrogradation when used in paper manufacture.

It is a further object of the present invention to provide methods of manufacturing paper which are faster and more efficient than existing methods.

It is a further object of the present invention to provide substitutes for starch in paper manufacturing that do not require costly chemical modification as does starch.

It is a further object of the present invention to provide methods for manufacturing paper that are more environmentally-friendly than existing methods.

It is a further object of the present invention to provide substitutes for thermoplastic molecules currently used in the coating step during paper manufacture.

SUMMARY OF THE INVENTION

The present invention provides glucans which can be used as substitutes for modified starch and latexes in paper manufacture. The present glucans are produced by the glucosyltransferase C ("GTF C") enzyme of the species *Streptococcus mutans*, and are functionally similar to the modified starch currently used in paper manufacture. The present glucans also exhibit similar physical properties to thermoplastic molecules currently used in the coating step during paper manufacture.

The present invention also provides methods of making paper utilizing the present glucans, input materials that are produced biologically. Thus, the present methods are more cost-effective and environmentally-friendly than current methods, which require input materials that produce chemical effluents.

DETAILED DESCRIPTION OF THE INVENTION

Seq ID No. 1—a partial gtfc cDNA sequence

Seq ID No. 2—the GTFC protein sequence encoded by Seq ID No. 1

As used herein "glucan" means a glucose polymer having linkages that are $\alpha(1\rightarrow3)$, $\alpha(1\rightarrow6)$ and branching $\alpha(1\rightarrow3,6)$.

As used herein "amyloplast" means starch accumulating organelle in plant storage tissue.

As used herein, "vacuole" means the cellular compartment bounded by the tonoplast membrane.

*Streptococcus mutans* is a species that is endogenous to the oral cavity and colonizes tooth enamel. See e.g. Kuramitsu, et al., "Characterization of Extracellular Glucosyl Transferase Activity of *Streptococcus mutans*," *Infect. Immun.;* Vol. 12(4); pp. 738–749; (1975); and Yamashita, et al., "Role of the *Streptococcus mutans gtf* Genes in Caries Induction in the Specific-Pathogen-Free Rat Model," *Infect. Immun.;* Vol. 61(9); pp. 3811–3817; (1993); both incorporated herein their entirety by reference. *Streptococcus mutans* species secrete the glucosyltransferase C ("GTF C") enzyme which utilizes dietary sucrose to make a variety of extracellular glucans. See e.g. Hanada, et al., "Isolation and Characterization of the *Streptococcus mutans gtfc* Gene, Coding for Synthesis of Both Soluble and Insoluble Glucans," *Infect. Immun.;* Vol. 56(8); pp. 1999–2005; (1988); and Kametaka, et al., "Purification and Characterization of Glucosyltransferase from *Streptococcus mutans* OMZ176 with Chromatofocusing," *Microbios;* Vol. 51(206); pp. 29–36; (1978); both incorporated herein in its entirety by reference.

Materials and Methods

Microorganisms. *S. mutans* GS-5 and *E. coli* MM294 (Bolivar, F. et al., "Plasmids of *Escherichia coli* as cloning vectors", *Methods Enzymol.* 65:245–267, 1979) and JM83 (Yanisch-Perron, C. et al., "Improved M13 phage cloning vectors and host strains: nucleotide sequence of the M13mp18 and pUC19 vectors", *Gene* 33:103–109, 1985) were maintained and grown routinely as previously described (Aoki, H. et al., "Cloning of a *Streptococcus mutans* gene coding for insoluble glucan synthesis", *Infect. Immun.* 53:587–594, 1986).

DNA manipulations. DNA isolation, endonuclease restriction, ligation, and transformation of competent *E. coli* cells were carried out as recently described (Aoki, supra). *S. mutans* transformations were carried out as originally described (Perry, D. et al. "Genetic transformation of putative cariogenic properties in *Streptococcus mutans*", *Infect. Immun.*41:722–727, 1983), and transformants were isolated on *mitis salivarius* agar plates containing erythromycin (10 μg/ml). Construction of the Pst I clone bank was recently described (Shiroza, T. et al., "Sequence analysis of the gtfB gene from *Streptococcus mutans*", *J. Bacteriol.* 169:4263–4270, 1987). Clones containing the gftC gene were initially identified following colony hybridization with a biotinylated 1.6-kilobase (kb) BamHI fragment from the gtfB gene (Aoki, supra).

Southern blot analysis. Southern blot analysis was carried out as recently described (Ueda, S. et al., "Molecular basis for the spontaneous generation of colonization defective mutants of *Streptococcus mutans*", *Mol. Microbiol.* 2:135–140, 1988) with biotinylated probes. The probes were constructed following nick translation as recommended by the supplier of biotin-dUTP (Bethesda Research Laboratories, Gaithersburg, Inc., Md.).

Results

Isolation of the gtfC gene. Based on recent nucleotide sequence data (Shiroza, supra), it was suggested that a gene sharing extensive homology with the gtfB gene was positioned immediately downstream from that gene. Furthermore, Southern blot analysis suggested that most of this homologous gene was contained within a 7.3-kb PstI fragment (Aoki, supra). Since this gene was also likely to code for GTF activity, an attempt was made to isolate it from a size-fractionated PstI clone bank of *S. mutans* GS-5 DNA constructed in vector pUC18. Screening of the clone bank with a probe containing a 1.6-kb BamHI fragment from the gtfB (Aoki, supra) gene revealed that 7 of approximately 600 clones reacted positively with the probe. One of these harbored a plasmid with the gtfB gene contained on a 6.4-kb PstI fragment. Restriction enzyme analysis of plasmids from two additional positive clones indicated that the plasmids each contained a 7.3-kb PstI fragment, indicating the presence of the homologous gene arranged in both orientations relative to the vector. One of the plasmids, pNH2 (FIG. 1), was used to isolate the intact homologous gene designated gtfC. *E. coli* strains harboring pNH2 were devoid of GTF activity.

Construction or the intact gtfC gene. Nucleotide sequence data (Shiroza, supra) suggested that plasmid pSU5 (FIG. 1), harboring the intact gtfB gene, also contained the amino-terminal sequences of the downstream homologous gene gtfC. Therefore, to construct the intact gtfC gene, we isolated a DNA fragment known to contain the amino-terminal sequences of the gene from M13-16N, an M13 chimeric bacteriophage isolated during the sequencing of the gtf gene and flanking regions (Shiroza, supra). A 1.1-kb SmaI-PstI fragment containing this region was isolated from an agarose gel and ligated to SmaI-PstI-digested plasmid pNH2dSP (pNH2 with an SphI fragment deleted) (FIG. 1). Following transformation, a clone expressing GTF activity was identified and shown to harbor plasmid pNH3. The enzyme appeared to synthesize significant amounts of both water-soluble and insoluble glucan when assayed in the standard assay system (Table 1). However, the presence of primer dextran was not required for enzymatic activity.

Expression of the gtfC gene in *E. coli*. The gtfc gene appeared to be expressed from its own promoter, since the addition of isopropyl-β-D-thiogalactopyranoside to *E. coli* transformants harboring plasmid pNH3 did not increase GTF activity (data not shown). In addition, when the gtfC gene was isolated on a 4.7-kb SphI-SmaI fragment from pNH3 and introduced into vector pUC19 (the gene was now oriented in the opposite direction relative to the lac promoter), GTF activity was still expressed. These results suggested that the gtfc gene fragment contained a promoter sequence which functioned in *E. coli*.

Both soluble and insoluble glucans are synthesized, and the proteins responsible have been isolated and characterized. See e.g. Aoki, et al., "Cloning of a *Streptococcus mutans* Glucosyltransferase Gene Coding for Insoluble Glucan Synthesis" *Infect. Immun.*, Vol. 53 (3); pp. 587–594; (1986); Shimamura, et al., "Identification of Amino Acid Residues in *Streptococcus mutans* Glucosyltransferases Influencing the Structure of the Glucan Produced," *J. Bacteriol.*; Vol. 176(16); pp. 4845–50; (1994); and Kametaka, et al., "Purification and Characterization of Glucosyltransferase from *Streptococcus mutans* OMZ176 with Chromatofocusing," *Microbios;* Vol. 51 (206); pp. 29–36; (1987); all incorporated herein their entirety by reference.

The proteins involved are large (~155 kDa) and catalyze the group transfer of the glucosyl portion of sucrose to an acceptor glucan via $\alpha(1\rightarrow3)$ and $\alpha(1\rightarrow6)$ linkages. See e.g. Wenham, et al., "Regulation of Glucosyl Transferase and Fructosyl Transferase Synthesis by Continuous Cultures of *Streptococcus mutans,*" *J. Gen Microbiol.;* Vol. 114 (Part 1); pp. 117–124; (1979); and Fu, et al., "Maltodextrin Acceptor Reactions of *Streptococcus mutans* 6715 glucosyltransferases," *Carbohydr. Res.;* Vol. 217; pp. 210–211; (1991); and Bhattacharjee, et al., "Formation of Alpha-$(1\rightarrow6)$, Alpha-$(1\rightarrow3)$, and Alpha $(1\rightarrow2)$ Glycosidic Linkages by Dextransucrase from *Streptococcus sanguis* in Acceptor-Dependent Reactions," *Carbohydr. Res.*, Vol. 242; pp. 191–201; (1993); all incorporated herein their entirety by reference.

The genes involved in glucan synthesis have been isolated and sequenced. See Shimamura, et al., cited hereinabove and Russel, et al., "Expression of a Gene for Glucan-binding Protein from *Streptococcus mutans* in *Escherichia coli,*" *J. Gen. Microbiol.;* Vol. 131(2); pp. 295–300; (1985); Russell, et al., "Characterization of Glucosyltransferase Expressed from a *Streptococcus sobrinus* Gene Cloned in *Escherichia coli,*" *J. Gen. Microbiol.;* Vol. 133(4); pp. 935–944; (1987); and Shiroza, et al., "Sequence Analysis of the gtfb Gene from *Streptococcus mutans,*" *J. Bacteriol.;* Vol. 169(9); pp. 4263–4270; (1987) see FIG. 2; all incorporated herein in their entirety by reference.

The structure of the glucans produced by the GTF C enzyme is quite heterogeneous with respect to the proportions of $\alpha(1\rightarrow3)$, $\alpha(1\rightarrow6)$ and $\alpha(1\rightarrow3,6)$ branches present in any given glucan. Transformation of genes which encode naturally occurring GTF C into plants, such as maize, provides amyloplasts and vacuoles with novel compositions.

GTF C enzyme activity incorporated into the amyloplast and/or vacuole leads to the accumulation of starch and glucan in the same amyloplast and/or vacuole. Retrogradation occurs as portions of starch molecules interact and subsequently form inter- or intra-chain helices. In a mixture of starch and glucans, the frequency of starch-starch interactions that lead to helix formation is diminished. A paste made from the mixed polymers is less prone to retrogradation as a result. This is especially true in the starch accumulation mutants envisioned as transformation targets where the relative proportion of starch is reduced.

Glucans produced in maize amyloplasts and/or vacuoles by the transgenic GTF C enzyme can function in paper processing without chemical modification, as required of starch. The polymer solution consequently has altered rheological properties and is less prone to retrogradation compared to starch. The glucans are branched and irregular and able to supplant modified starches with comparable or superior efficacy. They do not require any costly chemical modification as does starch. For coating applications, the present glucans exhibit thermoplastic properties in addition to the above advantages.

The wild type of GTF C is useful in producing glucans according to the present invention. The GTF C enzyme is well known. See e.g. Shimamura et al., and Hanada, et al., cited herein above. The glucans produced are particularly useful as substitutes for modified starches in the coating step of paper manufacture. The present glucans are also useful as substitutes for thermoplastic molecules such as latex (e.g. styrene butadiene). The subject glucans impact a high gloss finish on the paper and increase the ability of the paper to take on dyes and inks and improves the resolution in general on the printed sheet.

The glucans of the present invention are preferably produced in transgenic maize, potato, cassava, sweet potato, rye, barley, wheat, sorghum, oats, millet, triticale, sugarcane and rice. More preferably, the present glucans are produced in maize, potato, sugarcane, cassava, and sweet potato. Even more preferably, the present glucans are produced in maize and potato. Most preferably, the present glucans are produced in maize.

In a highly preferred embodiment of the present invention, maize lines deficient in starch biosynthesis are transformed with gtfC genes. Such lines may be naturally occurring maize mutants (i.e. $sh_2$, $bt_2$, $bt_1$) or transgenic maize engineered so as to accumulate low amounts of starch in the endosperm when compared to wild type maize. See e.g. Müller-Röber, et al., "Inhibition of the ADP-glucose Pyrophosphorylase in Transgenic Potatoes Leads to Sugar-Storing Tubers and Influences Tuber Formation and Expression of Tuber Storage Protein Genes," *The EMBO Journal;* Vol. 11(4); pp. 1229–1238; (1992); and Creech, "° Carbohydrate Synthesis in Maize," *Advances in Agronomy;* Vol. 20; pp. 275–322; (1968); both incorporated herein in their entirety by reference.

The production of the present glucans is performed according to methods of transformation that are well known in the art, and thus constitute no part of this invention. The compounds of the present invention are synthesized by insertion of an expression cassette containing a synthetic gene which, when transcribed and translated. yields a GTF enzyme that produces the desired glucan. Such empty expression cassettes, providing appropriate regulatory sequences for plant expression of the desired sequence, are also well-known, and the nucleotide sequence for the synthetic gene, either RNA or DNA, can readily be derived from the amino acid sequence for the protein using standard texts and the references provided. The above-mentioned synthetic genes preferably employ plant-preferred codons to enhance expression of the desired protein.

The following description further exemplifies the compositions of this invention and the methods of making and using them. However, it will be understood that other methods, known by those of ordinary skill in the art to be equivalent, can also be employed.

The genes which code for the present enzyme can be inserted into an appropriate expression cassette and introduced into cells of a plant species. Thus, an especially preferred embodiment of this method involves inserting into the genome of the plant a DNA sequence coding for a mutant or wild type in proper reading frame, together with transcription promoter and initiator sequences active in the plant. Transcription and translation of the DNA sequence under control of the regulatory sequences causes expression of the protein sequence at levels which provide an elevated amount of the protein in the tissues of the plant.

Synthetic DNA sequences can then be prepared which code for the appropriate sequence of amino acids of GTF C protein, and this synthetic DNA sequence can be inserted into an appropriate plant expression cassette.

Plant expression cassettes and vectors applicable in the present invention are well known in the art. By the term "expression cassette" is meant a complete set of control sequences including promoter, initiation, and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence.

By the term "vector" herein is meant a DNA sequence which is able to replicate and express a foreign gene in a host cell. Typically, the vector has one or more restriction endonuclease recognition sites which may be cut in a predictable fashion by use of the appropriate enzyme such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant".

A particularly preferred vector is a plasmid, by which is meant a circular double-stranded DNA molecule which is not a part of the chromosomes of the cell.

As mentioned above, both genomic DNA and cDNA encoding the gene of interest may be used in this invention. The gene of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

The expression cassette comprising the structural gene for a mutant of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. typhimurium,* and *Serratia marcescens*. Eukaryotic hosts such as yeast or filamentous fungi may also be used in this invention. Since these hosts are also microorganisms, it will be essential to ensure that plant promoters which do not cause expression of the protein in bacteria are used in the vector.

The isolated cloning vector will then be introduced into the plant cell using any convenient technique, including electroporation (in protoplasts), retroviruses, bombardment, and microinjection into cells from monocotyledonous or dicotyledonous plants in cell or tissue culture to provide transformed plant cells containing as foreign DNA at least one copy of the DNA sequence of the plant expression cassette. Using known techniques, protoplasts can be regenerated and cell or tissue culture can be regenerated to form whole fertile plants which carry and express the gene for a protein according to this invention. Accordingly, a highly preferred embodiment of the present invention is a transformed maize plant, the cells of which contain as foreign DNA at least one copy of the DNA sequence of an expression cassette of the GTF C protein.

It will also be appreciated by those of ordinary skill that the plant vectors provided herein can be incorporated into *Agrobacterium tumefaciens,* which can then be used to transfer the vector into susceptible plant cells, primarily from dicotyledonous species. Thus, this invention provides a method for introducing gtfC in *Agrobacterium tumefaciens*-susceptible dicotyledonous plants in which the expression cassette is introduced into the cells by infecting the cells with *Agrobacterium tumefaciens,* a plasmid of which has been modified to include a plant expression cassette of this invention.

For example, the potato plant can be transformed via *Agrobacterium tumefaciens* to produce the present glucans. The transformation cassette comprises a patatin promoter, followed by the gtfC coding sequence and the neomycin phosphotransferase polyadenylation site/terminator. See e.g. Utsumi, et al., "Expression and Accumulation for Normal and Modified Soybean Glycinins in Potato Tubers," *Plant Science;* Vol. 102(2); pp. 181–188; (1994); (Limerick); incorporated herein in its entirety by reference. The transgenic cassette is placed into a transformation vector. For example, BIN19, or derivatives thereof, are useful when transforming via *Agrobacterium tumefaciens*. See e.g. Visser, et al., "Transformation of Homozygous Diploid Potato with an *Agrobacterium-tumefaciens* Binary Vector System by Adventitious Shoot Regeneration on Leaf and Stem Segments," *Plant Mol. Biol.;* Vol. 12(3); pp. 329–338; (1989); incorporated herein in its entirety by reference.

For maize transformation vectors, the promoters include any promoter whose expression is specific and limited to endosperm cells. Included are those encoding either 22 kDa zein, opaque2, gamma zein and waxy. These lead into the gtfC gene and are followed by the endogenous terminator or the heterogeneous PINII terminator.

The GTF C protein is directed to the maize endosperm amyloplast using a suitable transit sequence. Transit sequences useful in directing the enzyme into the amyloplast for accumulation within the amyloplast include but are not limited to ribulose biphosphate carboxylase small subunit, waxy, brittle-1, and chlorophyll AB binding protein. The transit sequences are juxtaposed between the promoter and the gtfC coding sequence and fused in translational reading frame with the gtfC moiety.

Transit sequences useful in directing the enzyme into the vacuole for accumulation within the vacuole are well known in the art. For vacuolar targeting, see e.g. Ebskamp, et al., "Accumulation of Fructose Polymers in Transgenic Tobacco," *Bio/technology;* Vol. 12; pp. 272–275; (1994); incorporated herein in its entirety by reference.

For maize transformation and regeneration see e.g. Armstrong, C., (1994), "Regeneration of Plants from Somatic Cell Cultures: Applications for in vitro Genetic Manipulation," *The Maize Handbook,* Freeling, et al. eds, pp. 663–671; incorporated herein in its entirety by reference.

Once a given plant is transformed, the glucans synthesized can be isolated, by standard methods, known to one skilled in the art. The glucans thus obtained in the transgenic plant can be substituted for modified starches and utilized in the sizing and/or coating steps. For formulations useful in the coating step, see e.g. Heiser, et al., "Starch Formations," *Starch and Starch Products in Paper Coating;* Kearney, et al., eds., pp. 147–162; (1990); Tappi Press; incorporated herein in its entirety by reference.

The present glucans are utilized in an amount of from about 4 to about 15 weight percent, more preferably from about 5 to about 12 weight percent, also preferably from about 6 to about 8 weight percent. Weight percent is defined as grams of molecule per 100 ml coating solution.

The present glucans are used to replace the starch and/or latex molecules completely, or a starch-glucan or a latex-glucan mixture is used in the slurry. In the coating application, the glucan:starch ratio preferably ranges from about 10:90 to about 100:0; more preferably from about 40:60 to about 100:0; more preferably still from about 60:40 to about 100:0; most preferably about 100:0. The glucan-:latex ratio preferably ranges from about 10:90 to about 100:0; more preferably from about 40:60 to about 100:0; more preferably still from about 60:40 to about 100:0; most preferably about 100:0.

All publications cited in this application are indicative of the level of skill of those skilled in the art to which this invention pertains. All publications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

Deposit

The subject biological material has been deposited under conditions that assure that access to the biological material will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny are filed.

Upon allowance of any claims in the application, the Applicant(s) will make available to the public the subject biological material.

The biological material is on deposit with the American Type Culture Collection (ATCC), having been deposited under ATCC accession number PTA-1073. The ATCC is at 10801 University Boulevard, Manassas, Va. 20110-2209 USA (703) 365-2700. The biological material deposited with the ATCC were taken from the same clone deposits maintained by Pioneer Hi-Bred International, 800 Capital Square, 400 Locust Street, Des Moines, Iowa 50309-2340.

All restrictions imposed by the depositor on the availability of the deposited cultures to the public will be irrevocably removed upon the granting of a patent, except for that allowed under 37 C.F.R. 1.808(b). However, applicants have no authority to waive any restrictions imposed by law on the transfer of biological material or its transportation in commerce. It should be understood that the availability of a deposit does not constitute a license to practice the subject invention in derogation of patent rights granted by government action.

Further, the subject biological material deposits will be stored and made available to the public in accord with the provisions of the Budapest Treaty for the Deposit of Microorganisms. The deposit will be maintained for a term of at least thirty years or at least five years after the most recent request for a sample of the deposited biological material, whichever is longer.

Applicants have satisfied all the requirements of 37 C.F.R. 1.801–1.809, including providing an indication of the viability of the sample. The deposits will be replaced should it become necessary due to inviability, contamination, or loss of capability to function in the manner described in the specification.

What claimed is:

1. A transgenic plant cell containing a DNA molecule, the sequence of which is obtained from *Streptococcus mutans* and encodes a glucosyltransferase C enzyme, wherein the plant cell is derived from a plant selected from the group consisting of maize, potato, cassava, sweet potato and sugar cane.

2. The plant cell of claim 1 which is transformed by *Agrobacterium tumefaciens,* electroporation, retroviruses, bombardment or microinjection.

3. The plant cell of claim 1 wherein the enzyme produces a glucan in the amyloplast or vacuole of the plant cell.

4. The plant cell of claim 3 wherein the enzyme produces a glucan in the amyloplast of maize cells.

5. A transgenic plant regenerated from the plant cell of claim 1.

6. The plant of claim 5 wherein the plant is a maize line deficient in starch biosynthesis.

7. The plant of claim 6 wherein the plant is maize of genotype $sh_2$, $bt_2$ or $bt_1$.

8. A transgenic plant seed containing a DNA molecule, the sequence of which is obtained from *Streptococcus mutans* and encodes a glucosyltransferase C enzyme, wherein the plant seed is derived from a plant selected from the group consisting of maize, rye, barley, sugarcane, wheat, sorghum, oats, millet, triticale and rice.

9. The plant seed of claim 8 wherein the DNA molecule contains a promoter selected from the group consisting of 22 kDa zein, opaque2, gamma zein and waxy gene promoters.

* * * * *

SEQUENCE LISTING

```
<160> NUMBER OF SEQ ID NOS: 2

<210> SEQ ID NO 1
<211> LENGTH: 1243
<212> TYPE: DNA
<213> ORGANISM: Streptococcus mutans
<220> FEATURE:
<221> NAME/KEY: CDS
```

<222> LOCATION: (196)...(1245)

<400> SEQUENCE: 1

| | |
|---|---:|
| ttgttttttc gctctcttaa gttaattaag agggcgtttc tagggttagg agtttttaaat | 60 |
| attatttatt attttctaa aaaatgaaga atttcattat aaattaatta cgatacattg | 120 |
| tgcttttgtt atagaagtgt tacaatacta gtgttttata tcaaaacact aactctaact | 180 |

```
atttttggag gaaat atg gaa aag aaa gta cgt ttt aaa tta cgt aaa gta        231
            Met Glu Lys Lys Val Arg Phe Lys Leu Arg Lys Val
              1               5                  10 aag aaa aga tgg gtg aca gta tct att gct tca gct gta gtg act ttg         279
Lys Lys Arg Trp Val Thr Val Ser Ile Ala Ser Ala Val Val Thr Leu
         15                  20                  25 acc tct ctt tca gga agt cta gta aaa gca gat tca act gac gac cgt         327
Thr Ser Leu Ser Gly Ser Leu Val Lys Ala Asp Ser Thr Asp Asp Arg
 30                  35                  40 caa cag gcg gtt aca gaa tct cag gct agt ctt gtg acg aca agt gaa         375
Gln Gln Ala Val Thr Glu Ser Gln Ala Ser Leu Val Thr Thr Ser Glu
 45                  50                  55                  60 gca gca aaa gaa act ctg act gct act gat aca agt aca gca act tca         423
Ala Ala Lys Glu Thr Leu Thr Ala Thr Asp Thr Ser Thr Ala Thr Ser
             65                  70                  75 gca aca tct caa cca acc gcc act gtt act gat aat gtt tct aca aca         471
Ala Thr Ser Gln Pro Thr Ala Thr Val Thr Asp Asn Val Ser Thr Thr
         80                  85                  90 aac cag tct aca aat act act gct aat aca gct aat ttt gtc gtt aaa         519
Asn Gln Ser Thr Asn Thr Thr Ala Asn Thr Ala Asn Phe Val Val Lys
 95                 100                 105 cca aca aca act tcg gaa cag gct aaa act gat aat agt gac aaa ata         567
Pro Thr Thr Thr Ser Glu Gln Ala Lys Thr Asp Asn Ser Asp Lys Ile
110                 115                 120 att act aca tca aaa gcg gta aac cgt tta act gcg act ggt aaa ttt         615
Ile Thr Thr Ser Lys Ala Val Asn Arg Leu Thr Ala Thr Gly Lys Phe
125                 130                 135                 140 gtt cct gct aac aat aat act gca cat cca aaa act gtc act gat aaa         663
Val Pro Ala Asn Asn Asn Thr Ala His Pro Lys Thr Val Thr Asp Lys
                145                 150                 155 ata gtt cca ata aaa cca aag att ggt aaa tta aaa cag ccg tca tca         711
Ile Val Pro Ile Lys Pro Lys Ile Gly Lys Leu Lys Gln Pro Ser Ser
            160                 165                 170 ctt agt caa gat gat att gca gcc tta ggt aat gtc aaa aat atc aga         759
Leu Ser Gln Asp Asp Ile Ala Ala Leu Gly Asn Val Lys Asn Ile Arg
        175                 180                 185 aaa gtg aac ggt aaa tat tat tat tat aaa gaa gat gga act ctt caa         807
Lys Val Asn Gly Lys Tyr Tyr Tyr Tyr Lys Glu Asp Gly Thr Leu Gln
    190                 195                 200 aag aat tat gct tta aac att aat ggg aaa act ttc ttc ttt gat gaa         855
Lys Asn Tyr Ala Leu Asn Ile Asn Gly Lys Thr Phe Phe Phe Asp Glu
205                 210                 215                 220 aca gga gca tta tca aat aat act tta cct agt aaa aag ggt aat atc         903
Thr Gly Ala Leu Ser Asn Asn Thr Leu Pro Ser Lys Lys Gly Asn Ile
                225                 230                 235 act aat aat gat aac act aac agc ttt gct caa tat aat cag gtc tat         951
Thr Asn Asn Asp Asn Thr Asn Ser Phe Ala Gln Tyr Asn Gln Val Tyr
            240                 245                 250 agt aca gat gtt gca aac ttc gaa cat gtt gat cat tat ttg aca gcc         999
Ser Thr Asp Val Ala Asn Phe Glu His Val Asp His Tyr Leu Thr Ala
        255                 260                 265 gaa agt tgg tat cgt cct aaa tac atc tta aaa gat ggc aaa aca tgg        1047
```

```
Glu Ser Trp Tyr Arg Pro Lys Tyr Ile Leu Lys Asp Gly Lys Thr Trp
        270                 275                 280 aca cag tca aca gaa aaa gat ttc cgt ccc tta ctg atg aca tgg tgg    1095
Thr Gln Ser Thr Glu Lys Asp Phe Arg Pro Leu Leu Met Thr Trp Trp
285                 290                 295                 300 cct gac caa gaa acg cag cgt caa tat gtt aac tac atg aat gca cag    1143
Pro Asp Gln Glu Thr Gln Arg Gln Tyr Val Asn Tyr Met Asn Ala Gln
                305                 310                 315 ctt ggt att cat caa aca tac aat aca gca acc agt ccg ctt caa ttg    1191
Leu Gly Ile His Gln Thr Tyr Asn Thr Ala Thr Ser Pro Leu Gln Leu
            320                 325                 330 aat tta gct gct cag aca ata caa act aag atc gaa gaa aaa atc act    1239
Asn Leu Ala Ala Gln Thr Ile Gln Thr Lys Ile Glu Glu Lys Ile Thr
        335                 340                 345 gca g                                                              1243
Ala
```

<210> SEQ ID NO 2
<211> LENGTH: 349
<212> TYPE: PRT
<213> ORGANISM: Streptococcus mutans

<400> SEQUENCE: 2

```
Met Glu Lys Lys Val Arg Phe Lys Leu Arg Lys Val Lys Lys Arg Trp
1               5                   10                  15

Val Thr Val Ser Ile Ala Ser Ala Val Val Thr Leu Thr Ser Leu Ser
                20                  25                  30

Gly Ser Leu Val Lys Ala Asp Ser Thr Asp Arg Gln Gln Ala Val
            35                  40                  45

Thr Glu Ser Gln Ala Ser Leu Val Thr Thr Ser Glu Ala Ala Lys Glu
    50                  55                  60

Thr Leu Thr Ala Thr Asp Thr Ser Thr Ala Thr Ser Ala Thr Ser Gln
65                  70                  75                  80

Pro Thr Ala Thr Val Thr Asp Asn Val Ser Thr Thr Asn Gln Ser Thr
                85                  90                  95

Asn Thr Thr Ala Asn Thr Ala Asn Phe Val Lys Pro Thr Thr Thr
                100                 105                 110

Ser Glu Gln Ala Lys Thr Asp Asn Ser Asp Lys Ile Ile Thr Thr Ser
            115                 120                 125

Lys Ala Val Asn Arg Leu Thr Ala Thr Gly Lys Phe Val Pro Ala Asn
130                 135                 140

Asn Asn Thr Ala His Pro Lys Thr Val Thr Asp Lys Ile Val Pro Ile
145                 150                 155                 160

Lys Pro Lys Ile Gly Lys Leu Lys Gln Pro Ser Ser Leu Ser Gln Asp
                165                 170                 175

Asp Ile Ala Ala Leu Gly Asn Val Lys Asn Ile Arg Lys Val Asn Gly
            180                 185                 190

Lys Tyr Tyr Tyr Tyr Lys Glu Asp Gly Thr Leu Gln Lys Asn Tyr Ala
    195                 200                 205

Leu Asn Ile Asn Gly Lys Thr Phe Phe Asp Glu Thr Gly Ala Leu
210                 215                 220

Ser Asn Asn Thr Leu Pro Ser Lys Lys Gly Asn Ile Thr Asn Asn Asp
225                 230                 235                 240

Asn Thr Asn Ser Phe Ala Gln Tyr Asn Gln Val Tyr Ser Thr Asp Val
                245                 250                 255

Ala Asn Phe Glu His Val Asp His Tyr Leu Thr Ala Glu Ser Trp Tyr
```

-continued

```
                        260                     265                     270

Arg Pro Lys Tyr Ile Leu Lys Asp Gly Lys Thr Trp Thr Gln Ser Thr
        275                     280                     285

Glu Lys Asp Phe Arg Pro Leu Leu Met Thr Trp Trp Pro Asp Gln Glu
        290                     295                     300

Thr Gln Arg Gln Tyr Val Asn Tyr Met Asn Ala Gln Leu Gly Ile His
305                     310                     315                     320

Gln Thr Tyr Asn Thr Ala Thr Ser Pro Leu Gln Leu Asn Leu Ala Ala
                325                     330                     335

Gln Thr Ile Gln Thr Lys Ile Glu Glu Lys Ile Thr Ala
                340                     345
```